United States Patent [19]
Smith

[11] Patent Number: 4,917,085
[45] Date of Patent: Apr. 17, 1990

[54] DRIVE CUTTING CATHETER HAVING NEW AND IMPROVED DRIVE MOTOR

[75] Inventor: Kevin W. Smith, Miami, Fla.

[73] Assignee: Cordis Corporation, Miami, Fla.

[21] Appl. No.: 405,413

[22] Filed: Sep. 7, 1989

Related U.S. Application Data

[63] Continuation of Ser. No. 132,473, Dec. 14, 1987, abandoned.

[51] Int. Cl.⁴ .............................................. A61F 17/32
[52] U.S. Cl. ...................................... 606/159; 604/22
[58] Field of Search ............... 128/6, 305, 305.1, 751, 128/754, 755; 604/22

[56] References Cited

U.S. PATENT DOCUMENTS

| | | | |
|---|---|---|---|
| 3,614,953 | 10/1971 | Moss | 128/305.1 |
| 3,996,935 | 12/1976 | Banko | 604/22 |
| 4,207,874 | 6/1980 | Choy | 128/6 |
| 4,235,595 | 11/1980 | Arnegger | 128/305.1 |
| 4,445,509 | 5/1984 | Auth | 128/305 |
| 4,541,423 | 9/1985 | Barber | 128/305.1 |
| 4,589,412 | 5/1986 | Kensey | 128/305.1 |
| 4,631,052 | 12/1986 | Kensey | 604/22 |
| 4,646,738 | 3/1987 | Trott | 128/305 |
| 4,649,919 | 3/1987 | Thimsen et al. | 604/22 |
| 4,728,319 | 3/1988 | Masch | 604/22 |

Primary Examiner—Max Hindenburg
Attorney, Agent, or Firm—Watts, Hoffmann, Fisher & Heinke

[57] ABSTRACT

A drive catheter and a motor assembly to energize the catheter. A guidewire is inserted into the vicinity of an occluded blood vessel region and then the drive catheter and motor assembly are slipped over the guidewire. With the guidewire in place the motor is energized and a rotating distal tip portion pushed into contact with blood vessel deposits that block blood flow in the vessel to separate the deposits from the inner wall of the blood vessel.

8 Claims, 2 Drawing Sheets

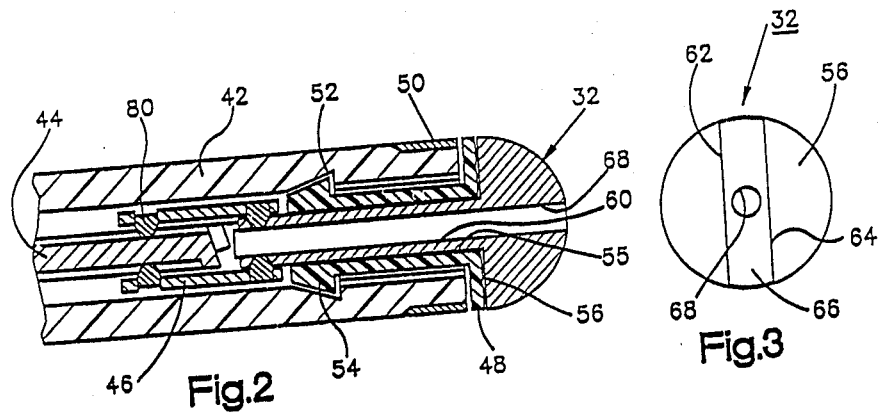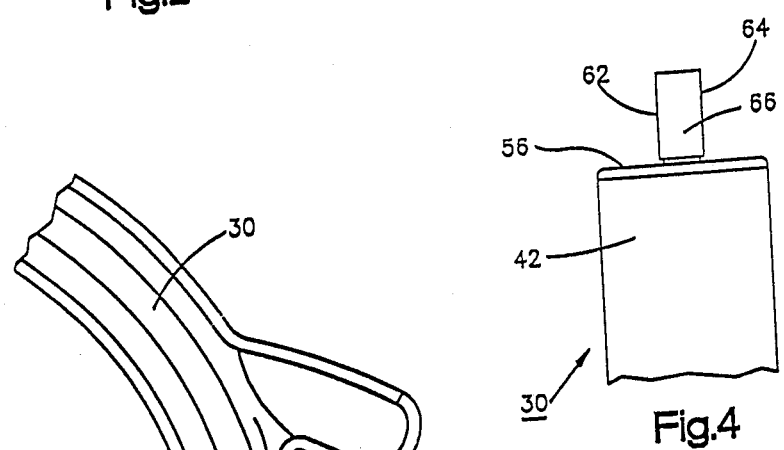

DRIVE CUTTING CATHETER HAVING NEW AND IMPROVED DRIVE MOTOR

This is a continuation of co-pending application Ser. No. 132,473, filed on Dec. 14, 1987, now abandoned.

TECHNICAL FIELD

The present invention relates to a catheter system for opening a totally or partially occluded blood vessel.

BACKGROUND ART

Arteriosclerosis is a condition where deposits build up along an inner surface of a blood vessel and cause a partial or, in extreme cases, a total blockage of the blood vessel. The increase in the number of coronary by-pass operations is some indication of the incidence with which the problem is encountered in older patients.

Prior art proposals recognize that one alternative to bypassing a partially or totally blocked region in a blood vessel is to open or widen the blocked blood vessel. One prior art technique for reopening a blocked blood vessel is to insert a balloon catheter inside the vessel to expand the vessel and either break loose deposits within the vessel or alternatively, increase the size of the lumen passing through those deposits.

An alternate proposal for opening a blocked blood vessel is to bring a high-speed rotating device into contact with occluded portions of the blood vessel. The rotating device produces cutting, abrading, or fluid turbulence to open the vessel and increase blood flow. One device intended for physically opening the blood vessel in this manner is disclosed in U.S. Pat. No. 3,614,953 to Moss entitled "Improvements In or Relating To Drills for Clearing Obstructions". In this patent, a high-speed motor rotates a flexible drive shaft connected to a cutting bit. The bit and flexible drive shaft are inserted into an occluded blood vessel so that when the bit is rotated at high speed and moved into contact with occluded regions it breaks loose deposits within the blood vessel.

A more recent prior art patent disclosing a similar system for opening a blocked blood vessel is disclosed in U.S. Pat. No. 4,445,509 to Auth entitled "Method and Apparatus for Removal of Enclosed Abnormal Deposits". This patent describes a differential cutting tool mounted at a distal end of a flexible shaft which can be inserted into an occluded blood vessel. Again, high speed rotation of the cutting tool causes the tool to remove abnormal deposits from inside the blood vessel. U.S. Pat. No. 4,589,412 to Kensey entitled "Method and Apparatus for Surgically Removing Remote Deposits" discloses a procedure for removing atherosclerotic plaque. A cutting tip is rotated by the application of fluid pressure through a multi-lumen catheter.

The proposals in the above-mentioned U.S. patents use high speed rotation of a distally located catheter tip to open a passageway through a blood vessel obstruction. Bringing a tip rotating at high speed into contact with blood vessel obstructions requires careful physician manipulation of the catheter. If the distal tip contacts the blood vessel wall with sufficient force the wall can be damaged or even punctured.

DISCLOSURE OF THE INVENTION

The present invention relates to a drive catheter that can be accurately guided to an occluded region of a blood vessel. The drive catheter is slipped over a guidewire which has been previously positioned within the blood vessel and energized to separate deposits within the blood vessel from the vessel wall.

In accordance with the invention a specially constructed motor includes a hollow output shaft supported in a motor body that extends completely through the motor body. An elongated cylindrical drive catheter has a center throughpassage extending from a proximal end of the catheter where it is attached to the motor shaft to a distal catheter tip. In combination, the drive catheter and motor define a combined throughpassage having a diameter sufficient to accommodate a flexible guidewire. The guidewire is positioned within the patient and subsequently utilized to position the elongated drive catheter relative to an obstructed region within the blood vessel prior to motor energization of the drive catheter tip.

The guidewire is maintained in position within the drive catheter during motor energization. This ensures that the drive catheter does not move from side to side in an uncontrolled fashion but rather remains aligned in a desired position by the guidewire.

In a preferred embodiment of the invention the rotating cylindrical drive of the drive catheter is surrounded by an outer plastic sheath or sleeve that does not rotate. A rotating drive shaft for imparting rotational motion to the tip passes through the sheath. Even if side to side movement of the rotating drive does occur during manipulation by the physician, the sheath and not the drive shaft contacts the inner wall surface of the blood vessel.

A preferred drive catheter drive shaft has two concentrically wound metal ribbons that spiral about a common axis from the proximal to distal end of the drive catheter. These metal ribbons are coupled to the motor output shaft and rotate in response to motor energization. The inner ribbon tends to expand outward under motor energization to provide a spacing between the center guidewire and the drive catheter. The outer ribbon tends to contract inward about the inner ribbon to provide a spacing between this outer ribbon and the stationary sheath.

In accordance with one embodiment of the invention, the drive catheter includes a side port for injecting contrast media into the drive catheter. The port is in fluid communication with a coupling interposed between the motor output shaft and the helically wound metal ribbon of the catheter drive shaft. This coupling defines a spiralling ridge that acts as a screw pump to deliver contrast medium or the like injected through the side port to the region between the stationary sheath and the catheter drive shaft.

At a distal end of the drive catheter, a rotating distal tip portion is coupled to the drive shaft and spaced from the non-rotating drive catheter sheath by a teflon bearing member. Since the guidewire extends completely through the drive catheter, the distal tip portion also defines an opening or throughpassage to accommodate the guidewire.

From the above it is appreciated that one object of the invention is a drive catheter for use in opening occluded regions of a blood vessel which can be guided and positioned with a conventional guidewire. This and other objects, advantages and features of the invention will become better understood from the detailed description of a preferred embodiment of the invention described in conjunction with the accompanying drawings.

BRIEF DESCRIPTION OF THE DRAWINGS

FIG. 1 is a schematic representation showing a drive catheter positioned in relation to a blood vessel occlusion;

FIG. 2 is a sectioned view of a distal portion of the FIG. 1 drive catheter;

FIG. 3 is an end elevation view of the drive catheter of FIG. 1;

FIG. 4 is a side elevation view of a proximal portion of the FIG. 1 drive catheter;

BEST MODE FOR CARRYING OUT THE INVENTION

Figure 5:
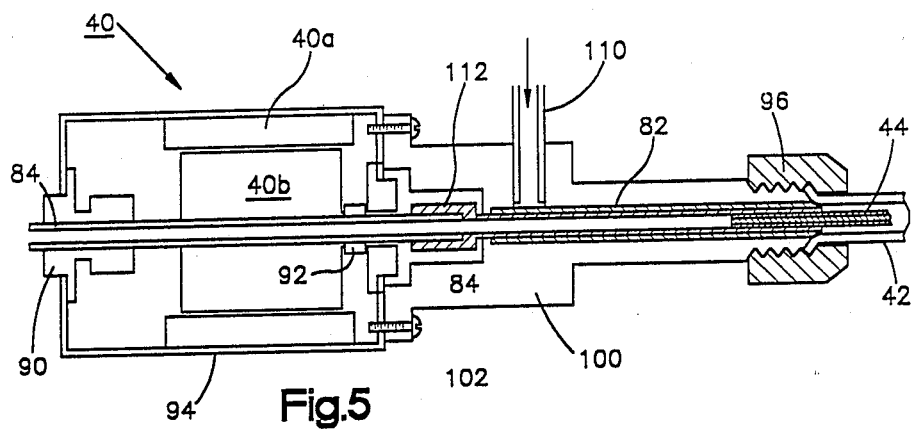
FIG. 5 is a partially sectioned view showing a proximal end of the drive catheter coupled to a motor for rotating a catheter drive shaft.

Turning now to the drawings, FIG. 1 schematically illustrates a blood vessel which has undesirable deposits 10 which line an inner wall 12 of the blood vessel. These deposits restrict blood flow through the blood vessel 12 and cause the patient's heart to work harder in delivering a sufficient amount of blood to the portion of the patient's body serviced by the blood vessel. In certain critical locations, such as blood vessels within the heart, if such a condition is left unattended, the long term prognosis for patient survival is not good.

A guidewire 20 schematically depicted in FIG. 1 is shown positioned to extend through the deposits 10. The guidewire 20 is of a conventional design and has been used in the prior art, for example, to position a balloon catheter for expanding a partially occluded blood vessel. Techniques for positioning a guidewire within a patient are well known in the prior art and typically utilize an x-ray imaging system that allows a physician inserting the guidewire to monitor the progress of the guidewire as it is pushed through the patient blood vessel. To help the physician in positioning the guidewire an extreme distal portion of the guidewire 20 is bent. This allows the physician to orient a guidewire distal tip and guide the tip into branching vessels that are encountered while routing the guidewire to the region of the deposits 10.

The guidewire 20 in FIG. 1 is used to guide a drive catheter 30 having a rotatable distal tip portion 32 into contact with the deposits 10. The guidewire 20 is inserted through the occluded region 10 and the drive catheter 30 slipped over the guidewire 20 until the distal tip 32 approaches the occluded blood vessel region 10. A motor 40 (FIG. 5) connected to a proximal portion of the drive catheter 30 outside the patient is then energized to rotate the distal tip 32 as the tip is brought into physical contact with the deposits 10. As the distal tip portion rotates at a controlled speed, the drive catheter 30 is pushed further into the patient along the guidewire and the rotating distal tip separates deposits 10 from the inner walls of the blood vessel 12. Throughout the procedure the guidewire 20 positions the distal tip portion 32 of the drive catheter 30 so that uncontrolled side to side movement of the drive catheter 30 is avoided.

The drive catheter 30 includes an outer plastic sheath 42 and inner drive shaft 44 (FIG. 2) that is connected to the distal tip 32 by a cylindrical coupling 46. The rotatable distal tip 32 engages a non-rotating plastic bearing 48 preferably constructed of Teflon (Registered Trademark). A cylindrical metal marker band 50 of a highly opaque material is connected to an extreme distal end of the sheath 42. This allows the physician to accurately monitor movement of the drive catheter 30 as it is pushed along the guidewire 20.

The outer plastic sheath 42 is preferably constructed having an imbedded braided wire core to stiffen the sheath 42. To construct the sheath 42 a first plastic layer is extruded onto a mandrel, the braided core then woven about the first plastic layer and then a second extruded layer applied which penetrates the wire core and is bonded to the first plastic extruded layer. At the extreme distal tip of the sheath 42, a cylindrical notch 52 is machined into an inner surface of the sheath 42 to accommodate a detent 54 in the plastic bearing 48. During assembly of the drive catheter 30, the bearing 48 is inserted into a distal opening in the sheath 42 until the detent 54 snaps into the cylindrical groove 52. When so positioned, the bearing 48 defines a throughpassage 55 to accommodate the rotatable tip 32. An extreme distal portion of the bearing 48 has approximately the same diameter as the sheath 42 and defines an outwardly facing annular bearing surface 56 that is exposed within the blood vessel.

The distal tip 32 includes an elongated cylindrical stem portion 60 that extends into the throughpassage 55 defined by the bearing 48. An exposed semi-circular portion of the distal tip 32 defines two opposed generally planar contact surfaces 62, 64 that engage the deposits 10 and an arcuate portion 66 interrupted at its center by a throughpassage 68 that extends through the elongated stem portion 60 of the distal tip 32 to the center of the sheath 42. The cylindrical coupling 46 that attaches the drive shaft 44 to the tip 32 has an inner diameter sufficient to slip over the stem portion 60 of the rotating tip 32 and is physically attached to the stem portion 60 by laser welding or the like.

Figure 7:
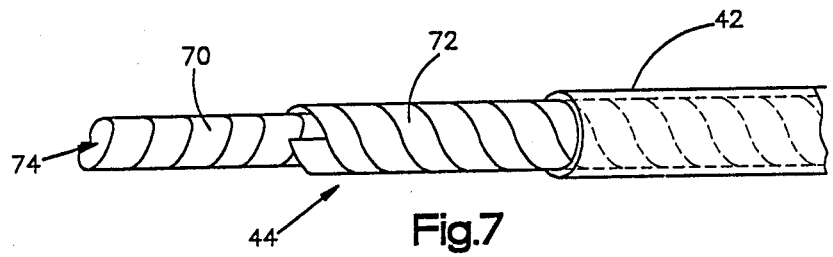
FIG. 7 is a perspective view showing inner and outer helically wound ribbon members comprising the catheter drive shaft.

As seen most clearly in FIG. 7, the drive shaft 44 for imparting rotational motion to the tip 32 is constructed of co-axial inner 70 and outer 72 flat ribbon wire wound in a helical pattern to define a throughpassage 74 for the guidewire 20. At the distal region of the drive catheter 30, the cylindrical coupling 46 is welded to the drive shaft 44. As seen in FIG. 2, a weld spot 80 extends through both the outer wire 72 and inner wire 70 to secure both wires of the drive shaft 44 to the distal tip 32. A preferred ribbon wire is constructed from stainless steel wound about an appropriately dimensioned mandrel, has a thickness of 0.002 inches and a width of approximately 0.01 inches. The mandrel for the outer ribbon wire 72 is slightly larger than for the inner ribbon wire 70.

Figure 6:
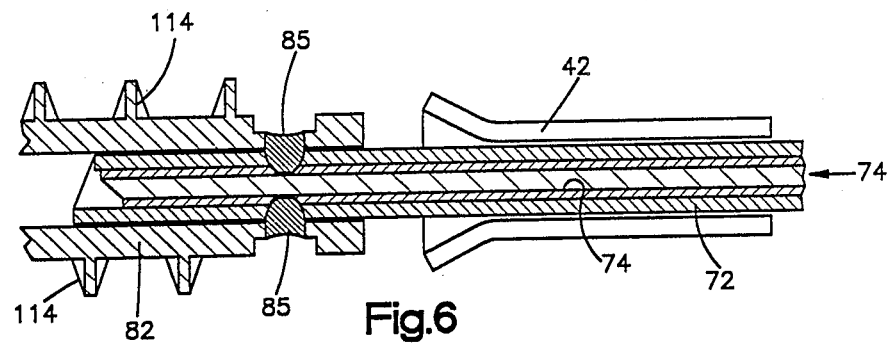
FIG. 6 is a sectional view on an enlarged scale showing a coupling interposed between the drive shaft and a motor output shaft.

A proximal drive coupling 82 connects an output shaft 84 of the motor 40 to the drive shaft 44 is depicted in FIG. 6. The drive coupling 82 is coupled to both the inner and outer ribbon wires 70, 72 of the drive shaft 74 by laser welding at regions 85 shown in FIG. 6. When energized by the motor, the coupling 82 imparts rotational motion to the drive shaft 44 in a sense to cause the inner ribbon 70 to unwind or unravel and expand leaving a larger gap for the guidewire 20 in the throughpassage 74. This tends to reduce frictional engagement between the inner wire 70 and guidewire 20. Due to the sense of the outer ribbon winding this rotation causes the outer wire 72 to tighten and therefore contract inward against the inner wire 70. This reduces frictional engagement between the drive shaft 44 and the outer sheath 42. In addition, this contraction of the outer wire 72 widens a throughpassage or spacing between the drive shaft 44 and an inner wall of the sheath 42. As discussed below, this spacing is used to accommodate the injection of contrast medium through the drive catheter to facilitate monitoring the removal of deposits during high speed rotation of the distal tip portion 32.

Turning now to FIG. 5, the motor 40 includes a hollow drive shaft 84 mounted in bearings 90, 92 and extending completely through a motor housing 94. The motor 40 housing 94 supports stationary field creating elements 40a. Radially inward from the field creating elements 40a are positioned rotating field responsive motor portions 40b coupled to the shaft 84. A preferred motor is a battery operated silver graphite brushed direct current motor having a variable speed control for rotating the hollow drive shaft 80 at variable speeds of from 20,000 to 100,000 rpm. A preferred rotational speed for the motor 40 is approximately 75,000 rpm. This motor is commercially available from Mora II Products, 21063 Cabot Blvd., Suite 6, Hayward, Calif. 94545.

An extreme proximal portion of the drive catheter 30 is depicted in FIGS. 5 and 6. The outer sheath 42 flares out at the extreme proximal portion and is fixed between a leur fitting 96 having a threaded opening and a corresponding threaded portion of a motor adapter 100 attached to the motor 40 with threaded connectors 102. The motor adapter 100 defines a side port 110 for injecting contrast fluid or the like into an hollow center region of the adapter 100. This spacing encloses the motor coupling 82. Contrast medium injected through the side port 110 is delivered to the spacing between the outer sheath 42 and the drive shaft 44 due to a pumping action achieved during rotation of the drive coupling 82. The drive coupling 82 is coupled to the hollow motor output shaft 80 by an intermediate coupling 112 for rotating the drive coupling 82. Threads or ridges 114 (FIG. 6) are defined in an outer surface of the coupling 82 so that fluid injected into the side port 10 is driven from the port 110 to the space between the sheath 42 and the drive shaft 44. In a preferred embodiment of the invention the pitch spacing along the threaded outside surface of the coupling 82 is constant but it is anticipated that a variable pitch thread could be utilized.

At the distal end (FIG. 2) the contrast medium passes the coupling 46 and flows past the bearing 48 to exit the drive catheter 30. Some of the contrast medium finds its way through the rotating ribbon wires 70, 72 to the center passageway 74 and at the distal end exits the opening 68 in the distal tip 32. In operation the physician positions the guidewire within a blood vessel and in particular positions the guidewire to enter and preferably traverse the region of deposits within the blood vessel. With the guidewire so positioned, the motor 40 with attached drive catheter 30 are removed from a sealed package and the distal tip 32 is slipped over the proximal portion of the guidewire. The drive catheter 30 is routed along the guidewire to the region of deposit build up. Movement of the drive catheter along the guidewire is monitored and in particular the marker tip 50 is readily visible by x-ray imaging equipment well known in the art. Once the distal tip 32 approaches the deposits 10, the motor is energized and the drive catheter and motor pushed further along the guidewire to bring the rotating distal tip portion of the drive catheter into contact with the deposits 10. Throughout the procedure, the physician can monitor movement of the drive catheter 30 both through monitoring the marker tip 50 as well as monitoring contrast medium injected through the side port in the motor adapter 100. This enables the physician to monitor the effectiveness of the procedure while the procedure is taking place rather than necessitating insertion of a separate catheter device for monitoring blood flow subsequent to the procedure.

The present invention has been described with a degree of particularity. It is the intent, however, that the invention include all modifications and alterations from the disclosed embodiment falling within the spirit or scope of the appended claims.

I claim:

1. Apparatus for opening an obstructed region of a blood vessel comprising:
    (a) a motor including a motor housing, bearings mounted within the motor housing, a drive shaft supported by the bearings for rotation with respect to the housing, field creating means fixed within the housing, and field responsive means coupled to the drive shaft for rotating the drive shaft with respect to the motor housing; said drive shaft defining a motor throughpassage extending completely through the motor housing;
    (b) a flexible elongated cylindrical drive catheter including a non-rotating outer sheath, an inner core that rotates within the outer sheath, and a distal tip coupled to a distal end of the core and extending beyond a distal end of the outer sheath; said core and distal tip defining a catheter throughpassage extending from a proximal end of the core, through the core and out the distal tip of the drive catheter;
    (c) structure including a body for coupling the motor housing to the outer sheath of the cylindrical drive catheter and defining a body passageway, a transmission positioned within the body passageway having one end coupled to an output shaft of the motor and having an opposite end coupled to the drive catheter core for imparting rotational motion from the motor drive shaft to the drive catheter core, said transmission defining a transmission throughpassage;
    (d) said motor drive shaft, transmission, rotatable core, and distal tip defining a combined throughpassage having a diameter sufficient to allow the drive catheter to be slipped over a guidewire already extending into the patient to route the distal tip into proximity to the obstructed region of the blood vessel and to be rotated by the motor to abrade deposits from an inner wall of the blood vessel.

2. The apparatus of claim 1 wherein the rotatable core of the drive catheter comprises first and second concentrically wound metal bands that spiral about a common axis and wherein the distal tip is coupled to the metal ribbons for rotation in response to rotation of the motor drive shaft.

3. The apparatus of claim 2 wherein a first inner metal band of the first and second concentrically wound metal bands tends to expand outward away from the common axis during rotation of the motor output shaft and a second outer band tends to contract inward toward the common axis during rotation of the output shaft.

4. The apparatus of claim 2 further comprising a bearing at the distal end of the drive catheter to space the distal tip from the sleeve.

5. The apparatus of claim 1 wherein in addition to coupling the motor housing to the drive catheter outer sheath the body further defines an infusion port for providing a fluid flow path to the body passageway to allow fluids to be injected into the body passageway and flow into the outer sheath of the drive catheter.

6. The apparatus of claim 5 wherein the transmission coupling the motor drive shaft to the core of the drive catheter defines an outer pumping surface of spiralling ridges for pumping fluid entering the body passageway into the outer sheath of the drive catheter.

7. A system for removing deposits from an inner wall of a subject blood vessel comprising:
   (a) a hand held motor including a motor housing, a rotatably mounted annular drive shaft extending through the motor housing which defines a drive shaft throughpassage, stationary field creating means coupled to the housing, and field responsive means mounted to the drive shaft for rotating the drive shaft in response to activation of the field creating means;
   (b) an elongated drive catheter including non-rotating outer sheath, a core that rotates within the outer sheath, and a distal tip coupled to the core to abrade the deposits from the blood vessel inner wall, said tip and core in combination defining a drive catheter throughpassage from a proximal end of the drive catheter passing through the distal tip that opens into the blood vessel with the drive catheter positioned within the subject; and
   (c) an intermediate coupling for transmitting rotational motion of the motor drive shaft to the rotatable core of the drive catheter, said intermediate coupling having an elongated transmission member that defines a center passageway and is attached at one end to the motor drive shaft and an opposite end to the core of the drive catheter and a coupling body connecting the motor housing to the non-rotating outer sheath of the drive catheter; said coupling body defining a body throughpassage to accomodate the transmission member and an infusion port in fluid communication with the body throughpassage to allow a fluid to be injected into the infusion port and pass through the coupling body to enter the non-rotating sheath of the drive catheter;
   (d) said drive shaft, rotatable core, and transmission member, in combination, defining a combined throughpassage to accommodate a guidewire for positioning the drive catheter relative the deposits in the subject blood vessel.

8. The system of claim 7 where the elongated transmission member comprises a spiral pump to move said fluid into the proximal end of the sheath as the motor drive shaft rotates the elongated transmission member.